US011160817B2

(12) United States Patent
Chow et al.

(10) Patent No.: US 11,160,817 B2
(45) Date of Patent: Nov. 2, 2021

(54) NUTRITIONAL COMPOSITIONS COMPRISING NEUROPROTECTIVE DIETARY OLIGOSACCHARIDES

(71) Applicant: ABBOTT LABORATORIES, Abbott Park, IL (US)

(72) Inventors: Jomay Chow, Westerville, OH (US); Matthew Panasevich, Urbana, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/653,686

(22) PCT Filed: Dec. 18, 2013

(86) PCT No.: PCT/US2013/076143
§ 371 (c)(1),
(2) Date: Jun. 18, 2015

(87) PCT Pub. No.: WO2014/100191
PCT Pub. Date: Jun. 26, 2014

(65) Prior Publication Data
US 2015/0342974 A1 Dec. 3, 2015

Related U.S. Application Data

(60) Provisional application No. 61/738,492, filed on Dec. 18, 2012.

(51) Int. Cl.
*A61K 31/702* (2006.01)
*A23C 9/20* (2006.01)
*A23L 33/10* (2016.01)
*A23L 33/21* (2016.01)
*A23L 33/00* (2016.01)
*A23P 10/40* (2016.01)

(52) U.S. Cl.
CPC ............ *A61K 31/702* (2013.01); *A23C 9/206* (2013.01); *A23L 33/10* (2016.08); *A23L 33/21* (2016.08); *A23L 33/40* (2016.08); *A23P 10/40* (2016.08); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,093,743 A * | 7/2000 | Lai | ............ | A61P 25/00 514/599 |
| 2004/0047856 A1* | 3/2004 | Williams | ............... | A61K 35/20 424/130.1 |
| 2008/0138435 A1* | 6/2008 | Van Den Berg | ........ | A61P 37/00 424/535 |
| 2011/0105609 A1* | 5/2011 | Shchepinov | ........... | A61K 31/20 514/549 |
| 2012/0172307 A1 | 7/2012 | Davis et al. | | |
| 2012/0172327 A1 | 7/2012 | Buck et al. | | |

FOREIGN PATENT DOCUMENTS

| | | | | |
|---|---|---|---|---|
| EP | 2609813 | | 7/2013 | |
| WO | WO 2012069416 A1 * | | 5/2012 | ............. A23L 1/296 |

OTHER PUBLICATIONS

Choi, H. S., Ko, Y. G., Lee, J. S., Kwon, O. Y., Kim, S. K., Cheong, C., . . . & Kang, S. A. (2010). Neuroprotective effects of consuming bovine colostrum after focal brain ischemia/reperfusion injury in rat model. Nutrition research and practice, 4(3), 196-202.*
Tao, N., DePeters, E. J., Freeman, S., German, J. B., Grimm, R., & Lebrilla, C. B. (2008). Bovine milk glycome. Journal of Dairy Science, 91(10), 3768-3778.*
Aldredge, D. L., Geronimo, M. R., Hua, S., Nwosu, C. C., Lebrilla, C. B., & Barile, D. (2013). Annotation and structural elucidation of bovine milk oligosaccharides and determination of novel fucosylated structures. Glycobiology, 23(6), 664-676. (Year: 2013).*
Chen, H., Yoshioka, H., Kim, G. S., Jung, J. E., Okami, N., Sakata, H., . . . & Chan, P. H. (2011). Oxidative stress in ischemic brain damage: mechanisms of cell death and potential molecular targets for neuroprotection. Antioxidants & redox signaling, 14(8), 1505-1517. (Year: 2011).*
Fiskum, G., Rosenthal, R. E., Vereczki, V., Martin, E., Hoffman, G. E., Chinopoulos, C., & Kowaltowski, A. (2004). Protection against ischemic brain injury by inhibition of mitochondrial oxidative stress. Journal of bioenergetics and biomembranes, 36(4), 347-352. (Year: 2004).*
Perrone, S., Szabó, M., Bellieni, C. V., Longini, M., Bangó, M., Kelen, D., . . . & Buonocore, G. (2010). Whole body hypothermia and oxidative stress in babies with hypoxic-ischemic brain injury. Pediatric neurology, 43(4), 236-240. (Year: 2010).*
Arciniegas, D. (2012). Hypoxic-ischemic brain injury. International Brain Injury Association, Alexandria www.internationalbrain.org/articles/hypoxicischemic-brain-injury. (Year: 2012).*
Vajda, F. J. E. (2004). Neuroprotection and neurodegenerative disease. In Alzheimer's Disease (pp. 235-243). Humana Press, Totowa, NJ. (Year: 2004).*
Wallin, C., Puka-Sundvall, M., Hagberg, H., Weber, S. G., & Sandberg, M. (2000). Alterations in glutathione and amino acid concentrations after hypoxia-ischemia in the immature rat brain. Developmental Brain Research, 125(1-2), 51-60. (Year: 2000).*
International Search Report and Written Opinion for PCT/US2013/076143 dated Apr. 2, 2014.

(Continued)

Primary Examiner — Dale R Miller
(74) Attorney, Agent, or Firm — Calfee, Halter & Griswold LLP

(57) ABSTRACT

A nutritional composition for use in providing a neuroprotective effect to an individual in need thereof which nutritional composition comprises at least one human milk oligosaccharide selected from lacto-N-neotetraose and 2'-fucosyllactose.

19 Claims, No Drawings

(56) References Cited

OTHER PUBLICATIONS

Buonocore et al., "Anti-oxidant strategies," Seminars in Fetal and Neonatal Medicine, Elsevier, vol. 12, No. 4, pp. 287-295, 2007.
De Vries et al., "Evolving Understanding of Hypoxic-Ischemic Encephalopathy in the Term Infant," Seminars in Pediatric Neurology, Elsevier, vol. 16, No. 4, pp. 216-225, 2009.
Diaz Heijtz et al., "Normal gut microbiota modulates brain development and behavior," Proceedings of the National Academy of Science, vol. 108, No. 7, pp. 3047-3052, Feb. 15, 2011.
Klein et al., "Oxidative stress in pneuomococcal meningitis: A future target for adjunctive therapy?" Progress in Neurobiology, Elsevier, vol. 80, No. 6, pp. 269-280, 2006.
Wang et al., "Dietary sialic acid supplementation improves learning and memory in piglets," The American Journal of Clinical Nutrition, vol. 85, No. 2, pp. 561-569, 2007.
Office Action in CN 201380066054.1 dated May 19, 2016.
Office Action in CN 201380066054.1 dated Apr. 13, 2017.
Notice of Reexamination in CN 201380066054.1 dated Oct. 17, 2018 (English Translation).
Reexamination Decision in CN 201380066054.1 dated Apr. 29, 2019 (English Translation).

\* cited by examiner

NUTRITIONAL COMPOSITIONS COMPRISING NEUROPROTECTIVE DIETARY OLIGOSACCHARIDES

CROSS-REFERENCE TO RELATED APPLICATIONS

This application is the U.S. national phase entry of PCT/US2013/076143, with an international filing date of Dec. 18, 2013, which claims priority to and any benefit of U.S. Provisional Application No. 61/738,492 filed Dec. 18, 2012, the entire contents of which are incorporated by reference in their entirety.

FIELD

The disclosure relates to nutritional compositions for use in providing a neuroprotective effect to an individual in need thereof. More particularly, the nutritional compositions include at least one human milk oligosaccharide selected from lacto-N-neotetraose and 2'-fucosyllactose.

BACKGROUND

Hypoxic-ischemic brain injury (HI-BI) is the functional and molecular damage to the brain resulting from hypoxia, ischemia, and/or cytotoxicity. Although this condition is one of the most common causes of death and disability among infants, it affects all age groups. In infants, HI-BI is often associated with severe prematurity, severe lung or heart disease, serious infections (especially meningitis or sepsis), trauma to the brain or skull, congenital malformations of the brain, or hypotension. Survivors are often faced with severe communication and feeding impairments as well as overall motor problems. Hypoxic-ischemic brain injury is also an important cause of morbidity and mortality in adults, and is often associated with other causal factors such as: cardiac arrest, respiratory arrest, near-drowning, near-hanging, and other forms of incomplete suffocation. In addition, brain injury from HI-BI can occur as a result of non-hemorrhagic stroke, although effects may be more localized.

BRIEF SUMMARY

A nutritional composition for use in providing a neuroprotective effect to an individual in need thereof wherein the nutritional composition comprises at least one human milk oligosaccharide selected from lacto-N-neotetraose and 2'-fucosyllactose.

DETAILED DESCRIPTION

Definitions

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO" as used herein, unless otherwise specified, refers generally to a number of complex carbohydrates found in human breast milk that can be in acidic or neutral form, and to precursors thereof. Exemplary non-limiting human milk oligosaccharides include 3'-sialyllactose (3SL), 6'-sialyllactose (6SL), lacto-N-neotetraose (LNnT), lacto-N-tetraose (LNT), disialylated lacto-N-tetraose (DSLNT), 3'-fucosyllactose (3FL), and 3'-sialyllactose (3SL), and 2'-fucosyllactose (2FL).

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which are suitable for oral consumption by a human. The terms "nutritional formulation" or "nutritional composition" do not include human breast milk.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "infant" or "term infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid, solid, semi-solid, and semi-liquid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "synthetic pediatric formula" as used herein, unless otherwise specified, refers to liquid, solid, semi-solid, and semi-liquid human milk replacements or substitutes that are suitable for consumption by an infant or toddler up to the age of 36 months (3 years). The synthetic formulas include components that are of semi-purified or purified origin. As used herein, unless otherwise specified, the terms "semi-purified" or "purified" refer to a material that has been prepared by purification of a natural material or by synthesis. The term "synthetic pediatric nutritional formula" does not include human breast milk.

The term "synthetic child formula" as used herein, unless otherwise specified, refers to liquid, solid, semi-solid, and semi-liquid human milk replacements or substitutes that are suitable for consumption by a child up to the age of 12 years. The synthetic formulas include components that are of semi-purified or purified origin. As used herein, unless otherwise specified, the terms "semi-purified" or "purified" refer to a material that has been prepared by purification of a natural material or by synthesis. The term "synthetic child nutritional formula" does not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Nitric oxide (NO) and excitatory amino acids are believed to contribute to HI-BI, thus nitric oxide synthase (NOS) inhibitors and N-methyl-D-aspartate (NMDA) glutamate receptor antagonists can offer protection against developing this condition. One example of a compound that has been shown to offer neuroprotection against HI-BI is the arginine catabolite, agmatine. Agmatine has been identified as a potential neurotransmitter or neuromodulator due to its affinity for brain receptors and has been shown to have modest affinity for the NMDA subclass of glutamate receptors. Furthermore, this compound has been shown to suppress nitric oxide production and inhibit all isoforms of NOS.

Although a majority of evidence supporting agmatine's neuroprotective effects involves direct perfusion of agmatine into the brain, other studies indicate that agmatine produced in the gut might also confer neuroprotective effects in the brain. For instance, when Piletz (Ann N Y Acad. Sci. 2003; 1009:64-74) measured brain agmatine concentrations in mice and in non-human primates, they found significant increases in brain agmatine concentrations coincident with peripheral injection concentrations at 50 and 300 mg/kg, a result suggesting that agmatine crosses the blood-brain barrier. Moreover, Haenisch (Am. J. Physiol. Gastrointest. Liver Physiol. 2008; 295(5):G1104-10) found that bacteria belonging to the Bacteroidetes, Firmicutes, Actinobacteria, and Proteobacteria phyla produced significant amounts of agmatine in the large intestine. Molderings (Ann N Y Acad. Sci. 2003; 1009:75-81) noted the presence of an energy-dependent agmatine-transport mechanism in several intestinal tumor cell lines, an observation that led Molderings (Ann N Y Acad. Sci. 2003; 1009:44-51) to conclude that agmatine in the large intestine could represent an important source of agmatine to tissues that utilize it.

It has been found that agmatine can be produced in the gut of a human with the already present intestinal flora by feeding particular human milk oligosaccharides (HMO). As shown in tables 1 and 2 and carried out as described in Example 51, anaerobic fermentation cultures of fecal samples taken from either breast-fed infants (BF) or formula-fed infants (FF) incubated with either lacto-N-neotetraose (LNnT) or 2'-fucosyllactose (2'FL) HMOs showed a dramatic increases in agmatine relative to a blank. This in vitro study shows that the consumption of selected HMOs will produce agmatine in vivo by the human's own intestinal flora.

TABLE 1

Increase of agmatine in breast fed infants

| | LNnT/ blank 0 h | LNnT/ blank 3 h | LNnT/ blank 6 h | 2'FL/ blank 0 h | 2'FL/ blank 3 h | 2'FL/ blank 6 h |
|---|---|---|---|---|---|---|
| agmatine | $9.52^a$ | 34.4 | 1.59 | 8.41 | 12.84 | 4.23 |

$^a$ $p \leq 0.05$ and $q < 0.10$ compared to blank.

TABLE 2

Increase of agmatine in formula fed infants

| | LNnT/ blank 0 h | LNnT/ blank 3 h | LNnT/ blank 6 h | 2'FL/ blank 0 h | 2'FL/ blank 3 h | 2'FL/ blank 6 h |
|---|---|---|---|---|---|---|
| agmatine | 2.12 | $61.77^a$ | $75.02^a$ | 1.63 | $68.89^a$ | $57.38^a$ |

$^a$ $p \leq 0.05$ and $q < 0.10$ compared to blank.

A nutritional composition for use in providing a neuroprotective effect to an individual in need thereof wherein the nutritional composition comprises at least one human milk oligosaccharide selected from lacto-N-neotetraose and 2'-fucosyllactose. Without being bound to a particular theory, it is believed that feeding an individual a nutritional composition comprising at least one human milk oligosaccharide selected from lacto-N-neotetraose and 2'-fucosyllactose will result in the intestinal flora consuming these compounds and producing a large increase of agmatine. The agmatine will be absorbed through the gut of the individual into their blood stream and then pass through the blood-brain barrier. The agmatine will then suppress nitric oxide production and inhibit all isoforms of NOS which will reduce the likelihood of HI-BI. Alternatively, agmatine may not be required to pass through the blood-brain barrier to have the desirable effect.

An individual in need of a neuroprotective effect is an individual at risk of HI-BI. Thus, an individual in need of a neuroprotective effect may be an infant born severely prematurely, or suffering from severe lung or heart disease, a serious infection (especially meningitis or sepsis), trauma to the brain or skull, congenital malformation(s) of the brain or hypotension. The individual may also be an adult who has undergone cardiac arrest, respiratory arrest, near-drowning, near-hanging, other forms of incomplete suffocation or non-hemorrhagic stroke.

Specific non-limiting examples of dietary oligosaccharides that may be additionally included individually or in combination in the nutritional compositions used in the method include: galactooligosaccharides, fructooligosaccharides, inulin, 6'-sialyllactose, lacto-N-tetraose, disialylated lacto-N-tetraose, 3'-fucosyllactose, or 3'-sialyllactose. In one embodiment, the method of providing a neuroprotective effect to an individual in need thereof comprises administering to the individual a nutritional composition comprising lacto-N-neotetraose. In another embodiment the nutritional composition comprises 2'-fucosyllactose.

In one embodiment, the nutritional composition is a liquid and comprises at least one human milk oligosaccharide selected from lacto-N-neotetraose and 2'-fucosyllactose in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than 2 mg/mL, and including from about 0.01 mg/mL to about 20 mg/mL, including from about 0.01 mg/mL to less than 2 mg/mL.

In a specific embodiment, the nutritional composition is a liquid and comprises lacto-N-neotetraose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than 2 mg/mL, including from about 0.01 mg/mL to about 20 mg/mL, and including from about 0.01 mg/mL to less than 2 mg/mL.

In a specific embodiment, the nutritional composition is a liquid and comprises 2'-fucosyllactose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than 2 mg/mL, including from about 0.01 mg/mL to about 20 mg/mL, and including from about 0.01 mg/mL to less than 2 mg/mL.

In one embodiment, the nutritional composition is a powder and comprises at least one human milk oligosaccharide selected from lacto-N-neotetraose and 2'-fucosyllactose, in an amount of from about 0.0005% to about 5%, including from about 0.01% to about 1%, by weight of the powder.

In a specific embodiment, the nutritional composition is a powder and comprises lacto-N-neotetraose, in an amount of from about 0.0005% to about 5%, such as from about 0.01% to about 1%, by weight of the powder.

In a specific embodiment, the nutritional composition is a powder and comprises 2'-fucosyllactose, in an amount of from about 0.0005% to about 5%, such as from about 0.01% to about 1%, by weight of the powder.

In a specific embodiment, the nutritional composition is a bar and comprises at least one human milk oligosaccharide selected from lacto-N-neotetraose and 2'-fucosyllactose, in an amount of from about 0.0005% to about 10%, including from about 0.01% to about 5%, by weight of the bar.

In a specific embodiment, the nutritional composition is a bar and comprises lacto-N-neotetraose, in an amount of from about 0.0005% to about 10%, such as from about 0.01% to about 5%, by weight of the bar.

In a specific embodiment, the nutritional composition is a bar and comprises 2'-fucosyllactose, in an amount of from about 0.0005% to about 10%, such as from about 0.01% to about 5%, by weight of the bar.

Human Milk Oligosaccharides (HMOs)

Human milk oligosaccharides are one of the main components of human breast milk, which contains, on average, 10 grams per liter of neutral oligosaccharides and 1 gram per liter of acidic oligosaccharides. The composition of human milk oligosaccharides is very complex and more than 200 different oligosaccharide-like structures are known.

HMOs may be included in the nutritional compositions alone, or in some embodiments, in combination with other immune enhancing factors (e.g., long chain polyunsaturated fatty acids, antioxidants, nucleotides, etc.). The HMO or HMOs may be isolated or enriched from milk(s) secreted by mammals including, but not limited to: human, bovine, ovine, porcine, or caprine species. The HMOs may also be produced via microbial fermentation, enzymatic processes, chemical synthesis, or combinations thereof.

In addition to HMOs described above, the nutritional composition may also comprise such HMOs as: acidic oligosaccharides, neutral oligosaccharides, n-acetylglucosylated oligosaccharides, and HMO precursors. Specific non-limiting examples of HMOs that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GlcNAc); L-fucose (Fuc); fucosyl oligosaccharides (i.e., lacto-N-fucopentaose I; lacto-N-fucopentaose II; 2'-fucosyllactose; 3'-fucosyllactose; lacto-N-fucopentaose III; lacto-N-difucohexaose I; and lactodifucotetraose); non-fucosylated, non-sialylated oligosaccharides (i.e., lacto-N-tetraose and lacto-N-neotetraose); sialyl oligosaccharides (i.e., 3'-sialyl-3-fucosyllactose; disialomonofucosyllacto-N-neohexaose; monofucosylmonosialyllacto-N-octaose (sialyl Lea); sialyl-lacto-N-fucohexaose II; disialyllacto-N-fucopentaose II; monofucosyldisialyllacto-N-tetraose); and sialyl fucosyl oligosaccharides (i.e., 2'-sialyllactose; 2-sialyllactosamine; 3'-sialyllactose; 3'-sialyllactosamine; 6'-sialyllactose; 6'-sialyllactosamine; sialyllacto-N-neotetraose c; monosialyllacto-N-hexaose; disialyllacto-N-hexaose I; monosialyllacto-N-neohexaose I; monosialyllacto-N-neohexaose II; disialyllacto-N-neohexaose; disialyllacto-N-tetraose; disialyllacto-N-hexaose II; sialyllacto-N-tetraose a; disialyllacto-N-hexaose I; and sialyllacto-N-tetraose b). Also useful are variants in which the glucose (Glc at the reducing end is replaced by N-acetylglucosamine (e.g., 2'-fucosyl-N-acetylglucosamine (2'FLNac) is such a variant to 2'-fucosyllactose). These HMOs are described more fully in U.S. Patent Application No. 2009/0098240, which is herein incorporated by reference in its entirety. Other suitable examples of HMOs that may be included in the compositions of the present disclosure include lacto-N-fucopentaose V, lacto-N-hexaose, para-lacto-N-hexaose, lacto-N-neohexaose, para-lacto-N-neohexaose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neoocataose, para-lacto-N-octanose, iso-lacto-N-octaose, lacto-N-octaose, monofucosyllacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-decaose, trifucosyllacto-N-neooctaose, trifucosyllacto-N-octaose, trifucosyl-iso-lacto-N-octaose, lacto-N-difuco-hexaose II, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof. Particularly suitable nutritional compositions include at least one of the following HMOs or HMO precursors: sialic acid (SA); 3'-sialyllactose (3'SL); 6'-sialyllactose (6'SL); 2'-fucosyllactose (2'FL); 3'-fucosyllactose (3'FL); lacto-N-tetraose and lacto-N-neotetraose (LNnT), and in particular, combinations of 6'SL and 3'SL; combinations of 3'FL and SA; combinations of 2'FL and 3'FL; combinations of 2'FL, 3'SL, and 6'SL; combinations of 3'SL, 3'FL, and LNnT; and combinations of 6'SL, 2'FL, and LNnT.

Other exemplary combinations include: SA, 3'SL, 6'SL, 3'FL, 2'FL, and LNnT; 3'SL, 6'SL, 3'FL, 2'FL, and LNnT; SA, 6'SL, 3'FL, 2'FL, and LNnT; SA, 3'SL, 3'FL, 2'FL, and LNnT; SA, 3'SL, 6'SL, 2'FL, and LNnT; SA, 3'SL, 6'SL, 3'FL, and LNnT; SA, 3'SL, 6'SL, 3'FL, and 2'FL; SA and 3'SL; SA and 6'SL; SA and 2'FL; SA and LNnT; SA, 3'SL, and 6'SL; SA, 3'SL and 3'FL; SA, 3'SL and 2'FL; SA, 3'SL and LNnT; SA, 6'SL and 3'FL; SA, 6'SL, and 2'FL; SA, 6'SL, and LNnT; SA, 3'FL, and 2'FL; SA, 3'FL, and LNnT; SA, 2'FL, and LNnT; SA, 3'SL, 6'SL, and 3'FL; SA, 3'SL, 6'SL and 2'FL; SA, 3'SL, 6'SL, and LNnT; SA, 3'SL, 3'FL, and 2'FL; SA, 3'SL, 3'FL, and LNnT; SA, 3'SL, 2'FL, and LNnT; SA, 6'SL, 3'FL, and 2'FL; SA, 6'SL, 2'FL, and LNnT; SA, 6'SL, 3'FL, and LNnT; SA, 3'FL, 2'FL, and LNnT; SA, 6'SL, 2'FL, and LNnT; SA, 3'SL, 3'FL, 2'FL, and LNnT; SA, 6'SL, 3'FL, 2'FL, and LNnT; SA, 3'SL, 6'SL, 3'FL, and LNnT; SA, 3'SL, 3'FL, 2'FL, and LNnT; SA, 3'SL, 6'SL, 2'FL, and LNnT; 3'SL, 6'SL, 3'FL, and 2'FL; 3'SL, 6'SL, 2'FL, and LNnT; 3'SL, 3'FL, 2'FL, and LNnT; 3'SL, 6'SL, 3'FL, and LNnT; 3'SL, 6'SL, and 3'FL; 3'SL, 3'FL, and 2'FL; 3'SL, 2'FL, and LNnT; 3'SL, 6'SL, and 2'FL; 3'SL, 6'SL, and LNnT; 3'SL and 3'FL; 3'SL and 2'FL; 3'SL and LNnT; 6'SL and 3'FL; 6'SL and 2'FL; 6'SL and LNnT; 6'SL, 3'FL, and LNnT; 6'SL, 3'FL, 2'FL, and LNnT; 3'FL, 2'FL, and LNnT; 3'FL and LNnT; and 2'FL and LNnT.

Long Chain Polyunsaturated Fatty Acids (LCPUFAs)

The nutritional composition may include LCPUFAs to provide nutritional support, as well as to reduce oxidative stress and enhance growth and functional development of the intestinal epithelium and associated immune cell populations. In some embodiments, the nutritional composition includes a combination of one or more HMOs and one or more LCPUFAs such that the composition provides a synergistic benefit to the end user, such as a synergistic benefit in modulating anti-viral immune responses and dampening inflammation. In some embodiments, the HMO or HMOs used in combination with the LCPUFAs to provide the synergistic effect are acidic HMOs.

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), docosapentaenoic acid (DPA), arachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, DPA, and combinations thereof.

In order to reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, in esterified form or as a mixture of one or more of the above, preferably in triglyceride form.

The nutritional compositions may comprise total concentrations of LCPUFA of from about 0.01 mM to about 10 mM, and including from about 0.01 mM to about 1 mM.

Alternatively, the nutritional compositions may comprise total concentrations of LCPUFA of from about 0.001 g/L to about 1 g/L.

In one embodiment, the nutritional compositions include total long chain ω-6 fatty acids in a concentration of from about 100 to about 425 mg/L or from about 12 to about 53 mg per 100 kcals and/or further include total long chain ω-3 fatty acids in a concentration of from about 40 to about 185 mg/L or from about 5 to about 23 mg per 100 kcals. In one specific embodiment, the ratio of long chain ω-6 fatty acids to long chain ω-3 fatty acids in the nutritional compositions ranges from about 2:1 to about 3:1, preferably about 2.5:1.

In one specific embodiment, the nutritional compositions include DHA in a concentration of from about 0.025 mg/mL to about 0.130 mg/mL or from about 3 to about 16 mg per 100 kcals. In another embodiment, the nutritional compositions include ARA in a concentration of from about 0.080 mg/mL to about 0.250 mg/mL or from about 10 to about 31 mg per 100 kcals. In yet another embodiment, the nutritional compositions include combinations of DHA and ARA such that the ratio of DHA to ARA ranges from about 1:4 to about 1:2.

Antioxidants

The nutritional compositions may comprise one or more antioxidants (and optionally LCPUFAs and/or nucleotides also) to provide nutritional support, as well as to reduce oxidative stress. In some embodiments, the nutritional composition includes a combination of HMOs and antioxidants such that the composition provides a synergistic benefit to the end user, such as a synergistic benefit in modulating anti-viral immune responses and dampening inflammation. In some embodiments, the HMO or HMOs is used in combination with carotenoids (and specifically lutein, beta-carotene, zeaxanthin and/or lycopene) to provide the synergistic effect.

Any antioxidants suitable for oral administration may be included for use in the nutritional compositions of the present disclosure, including, for example, vitamin A, vitamin E, vitamin C, retinol, tocopherol, and carotenoids, including lutein, beta-carotene, zeaxanthin, and lycopene, and combinations thereof, for example.

The antioxidants for use in the nutritional compositions may be used with the HMOs, alone, or in combination with HMOs and LCPUFAs and/or nucleotides. In one embodiment, the antioxidants for use in the nutritional compositions include carotenoids. In one embodiment the carotenoids are lutein, lycopene, zeaxanthin and/or beta-carotene. Nutritional compositions containing these combinations, as selected and defined herein, can be used to modulate inflammation and/or levels of C-reactive protein in preterm and term infants.

The nutritional compositions may comprise at least one of lutein, lycopene, zeaxanthin, and beta-carotene to provide a total amount of carotenoid of from about 0.001 µg/mL to about 10 µg/mL. In one embodiment, the nutritional compositions may comprise lutein in an amount of from about 0.001 µg/mL to about 10 µg/mL, including from about 0.001 µg/mL to about 5 µg/mL, including from about 0.001 µg/mL to about 0.0190 µg/mL, including from about 0.001 µg/mL to about 0.0140 µg/mL, and also including from about 0.044 µg/mL to about 5 µg/mL of lutein. In another embodiment, the nutritional compositions comprise from about 0.001 µg/mL to about 10 µg/mL, including from about 0.001 µg/mL to about 5 µg/mL, including from about 0.001 µg/mL to about 0.0130 µg/mL, including from about 0.001 µg/mL to about 0.0075 µg/mL, and also including from about 0.0185 µg/mL to about 5 µg/mL of lycopene. In another embodiment, the nutritional compositions comprise from about 1 µg/mL to about 10 µg/mL, including from about 1 µg/mL to about 5 µg/mL, including from about 0.001 µg/mL to about 0.025 µg/mL, including from about 0.001 µg/mL to about 0.011 µg/mL, and also including from about 0.034 µg/mL to about 5 µg/mL of beta-carotene. Any combination of these amounts of beta-carotene, lutein, zeaxanthin, and lycopene can be included in the nutritional compositions. Other carotenoids may optionally be included in the nutritional compositions. Any one or all of the carotenoids included in the nutritional compositions may be from a natural source, or artificially synthesized.

Each of the carotenoids in the selected combinations can be obtained from any known or otherwise suitable material source for use in nutritional compositions, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), FloraGLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.).

Nucleotides

The nutritional compositions may comprise nucleotides and/or nucleotide precursors selected from nucleosides, purine bases, pyrimidine bases, ribose, and deoxyribose. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt. In some embodiments, the nutritional composition includes a combination of HMOs and nucleotides such that the composition provides a synergistic benefit to the end user, such as a synergistic benefit in modulating anti-viral immune responses and dampening inflammation and/or improving intestinal barrier integrity.

Incorporation of nucleotides in the nutritional compositions of the present disclosure improves intestinal barrier integrity and/or maturation, which is beneficial to preterm and term infants who have less developed intestinal flora and hence a slower maturing intestinal barrier.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, such as cytidine 5'-monophosphate, uridine 5'-monophosphate, adenosine 5'-monophosphate, guanosine 5'-monophosphate, and inosine 5'-monophosphate.

The nucleotides are present in the nutritional compositions in total amounts of nucleotides of at least about 5 mg/L, including at least about 10 mg/L, including from about 10 mg/L to about 200 mg/L, including from about 42 mg/L to about 102 mg/L, and including at least about 72 mg/L of the nutritional product.

In one specific embodiment when the nutritional composition is a nutritional powder, the nucleotide may be present at a level of at least about 0.007%, including from about 0.0078% to about 0.1556%, and including about 0.056% (by weight of the nutritional powder), or at least about 0.007 grams, including from about 0.0078 grams to about 0.1556 grams, and including about 0.056 grams of nucleotide per 100 grams of nutritional powder.

In another specific embodiment, when the nutritional composition is a ready-to-feed nutritional liquid, the nucleotide is present at a level of at least about 0.001%, including from about 0.001% to about 0.0197%, and including about 0.0071% (by weight of the nutritional liquid), or at least about 0.001 grams, including from about 0.001 grams to about 0.0197 grams, and including about 0.0071 grams of nucleotide per 100 grams of ready-to-feed nutritional liquid.

In another specific embodiment when the nutritional composition is a concentrated nutritional liquid, the nucleotide is present at a level of at least about 0.0019%, including from about 0.0019% to about 0.0382%, and including about 0.0138% (by weight of the nutritional liquid), or at least about 0.0019 grams, including from about 0.0019 grams to about 0.0382 grams, and including about 0.0138 grams of nucleotide per 100 grams of concentrated nutritional liquid.

Macronutrients

The nutritional compositions may be formulated to include at least one of protein, fat, and carbohydrate. In many embodiments, the nutritional compositions will contain an HMO or HMOs and comprise at least one of fat, protein, or carbohydrate.

Although total concentrations or amounts of the fat, protein, and carbohydrates may vary depending upon the product type (i.e., human milk fortifier, preterm infant formula, infant formula, etc.), product form (i.e., nutritional solid, powder, ready-to-feed liquid, concentrated liquid, or nutritional bar) and targeted dietary needs of the intended user, such concentrations or amounts most typically fall within one of the following embodied ranges, inclusive of any other essential fat, protein, and/or carbohydrate ingredients as described herein.

For the liquid formulas, carbohydrate concentrations most typically range from about 5% to about 40%, including from about 7% to about 30%, including from about 10% to about 25%, by weight; fat concentrations most typically range from about 1% to about 30%, including from about 2% to about 15%, and also including from about 3% to about 10%, by weight; and protein concentrations most typically range from about 0.5% to about 30%, including from about 1% to about 15%, and also including from about 2% to about 10%, by weight.

For the liquid human milk fortifiers, carbohydrate concentrations most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

The amount of carbohydrates, fats, and/or proteins in any of the liquid nutritional compositions described herein may also be characterized in addition to, or in the alternative, as a percentage of total calories in the liquid nutritional composition as set forth in the following tables. These macronutrients for liquid nutritional compositions used in the methods of the present disclosure are most typically formulated within any of the caloric ranges (embodiments A-F) described in the following table (each numerical value is preceded by the term "about").

TABLE 3

| Nutrient | Embodiment A (% Total Cal) | Embodiment B (% Total Cal) | Embodiment C (% Total Cal) |
| --- | --- | --- | --- |
| Carbohydrate | 0-98 | 2-96 | 10-75 |
| Protein | 0-98 | 2-96 | 5-70 |
| Fat | 0-98 | 2-96 | 20-85 |

TABLE 4

| Nutrient | Embodiment D (% Total Cal) | Embodiment E (% Total Cal) | Embodiment F (% Total Cal) |
| --- | --- | --- | --- |
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

TABLE 5

| Nutrient | Embodiment G (% Total Cal) | Embodiment H (% Total Cal) | Embodiment I (% Total Cal) |
| --- | --- | --- | --- |
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered adult, child, toddler, newborn, pediatric, preterm, or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, including from about 20% to about 50% by weight of the human milk fortifier.

The total amount or concentration of fat, carbohydrate, and protein, in the powdered nutritional compositions used in the methods of the present disclosure can vary considerably depending upon the selected composition and dietary or medical needs of the intended user. Additional suitable examples of micronutrient concentrations are set forth below. In this context, the total amount or concentration refers to all fat, carbohydrate, and protein sources in the powdered product. For powdered nutritional compositions, such total amounts or concentrations are most typically and preferably formulated within any of the embodied ranges described in the following table (each numerical value is preceded by the term "about").

TABLE 6

| Nutrient % Total Cal. | Embodiment J (% Total Cal) | Embodiment K (% Total Cal) | Embodiment L (% Total Cal) |
| --- | --- | --- | --- |
| Carbohydrate | 1-85 | 30-60 | 35-55 |
| Fat | 5-70 | 20-60 | 25-50 |
| Protein | 2-75 | 5-50 | 7-40 |

When the nutritional product is a nutritional bar, the protein component is present in an amount of from about 5% to about 45%, including from about 15% to about 35%, and including from about 20% to about 30% by weight of the nutritional bar; the fat component is present in an amount of from about 2% to about 25%, including from about 5% to about 20%, and including from about 10% to about 15% by weight of the nutritional bar; and the carbohydrate component is present in an amount of from about 2% to about 25%, including from about 5% to about 20%, including from about 5% to about 15% by weight of the nutritional bar.

Fat

The nutritional compositions may comprise a source or sources of fat. Suitable additional sources of fat for use herein include any fat or fat source that is suitable for use in an oral nutritional product and is compatible with the essential elements and features of such products. For example, in one specific embodiment, the additional fat is derived from long chain polyunsaturated fatty acids and/or short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions may comprise protein. Any protein source that is suitable for use in oral nutritional compositions and is compatible with the essential elements and features of such products is suitable for use in the nutritional compositions.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

Carbohydrate

The nutritional composition may comprise any carbohydrates that are suitable for use in an oral nutritional product and are compatible with the essential elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The nutritional compositions may comprise other optional ingredients that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, and other prebiotics (e.g., other neutral or acidic HMOs, inulin, oligofructose, polydextrose, pectin hydrolysate, and gums), probiotics (e.g., *B. animalis* subsp. *lactis* BB-12, *B. lactis* HN019, *B. lactis* Bi07, *L. rhamnosus* GG, *L. rhamnosus* HN001, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), postbiotics (metabolites of probiotics), long chain polyunsaturated fatty acids (DHA, ARA, DPA, EPA, etc.), nucleotides, antioxidant/anti-inflammatory compounds including tocopherols, caroteinoids, ascorbate/vitamin C, ascorbyl palmitate, polyphenols (e.g., curcumin), glutathione, and superoxide dismutase (melon), milk protein of human and/or bovine origin, soy protein, pea protein, other bioactive factors (e.g., growth hormones, cytokines, TFG-β) of human and/or bovine origin, tributyrin or other SCFA-containing mono-, di-, or triglycerides, human milk-derived lipids, free amino acids or peptides (e.g., HMB, arginine, leucine, and/or glutamine), lactose, other water- and fat-soluble vitamins, minerals, and trace elements, pharmaceutical actives, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isomalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from about 0.1% to about 10%, and also including from about 1% to about 6%, by weight of the nutritional product. Optional artificial sweetener concentrations may range from about 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Methods of Manufacture

The nutritional composition may be prepared by any known or otherwise effective manufacturing technique for preparing the selected product solid or liquid form. Many such techniques are known for any given product form such as nutritional liquids, powders, and nutritional bars, and can easily be applied by one of ordinary skill in the art to the nutritional compositions described herein.

The nutritional composition can be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective technique, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

The nutritional composition may be in the form of a bar. In one suitable manufacturing process, for example, the safflower oil, lecithin, glycerin, water, and flavors are added to a mixer. The dry powder ingredients and the vitamin mineral premix is added to the mixer and mixed for 1 minute. Corn syrup (heated to 95-105° F.) is added to the mixer and mixed for 2 minutes. Soy crisps and marshmallow bits are added to the mixer and mixed for 2 minutes. Chilled chocolate drops are added to the mixer and mixed for 1 minute. The mixture is formed into bars. A coating (preheated to 95-100° F.) is applied. Many different ingredients and mixing procedures may be used to make a nutritional bar.

Other suitable methods for making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application 20030118703 A1 (Nguyen, et al.), which descriptions are incorporated herein by reference to the extent that they are consistent herewith.

Product Form

The nutritional composition may be formulated and administered in any known or otherwise suitable oral product form. Any solid, liquid, semi-solid, semi-liquid, or powder product form, including combinations or variations thereof, are suitable for use herein, provided that such forms allow for safe and effective oral delivery to the individual of the ingredients as also defined herein.

The composition may be formulated as dietary product forms, which are defined herein as those embodiments comprising the ingredients of the present disclosure in a product form that then contains at least one of fat, protein, and carbohydrate, and preferably also contains vitamins, minerals, or combinations thereof.

The nutritional compositions may be formulated with sufficient kinds and amounts of nutrients to provide a sole, primary, or supplemental source of nutrition, or to provide a specialized nutritional product for use in individuals afflicted with specific conditions or with a targeted nutritional benefit as described below.

Some exemplary, non-limiting, examples of specific products that may be suitable for use in accordance with the present disclosure include preterm infant formulas, term infant formulas, human milk fortifiers, pediatric formulas, adult nutritional formulas, older adult nutritional formulas, medical formulas, geriatric nutritional formulas, diabetic nutritional formulas, nutritional bar, and the like.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to 95% by weight of water, including from about 50% to 95%, also including from about 60% to about 90%, and also including from about 70% to about 85%, of water by weight of the nutritional emulsions. The nutritional emulsions may have a variety of product densities, but most typically have a density greater than 1.03 g/mL, including greater than 1.04 g/mL, including greater than 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least 1 mL, or even at least 2 mL, or even at least 5 mL, or even at least 10 mL, or even at least 25 mL, including ranges from 1 mL to about 300 mL, including from about 4 mL to about 250 mL, and including from about 10 mL to about 240 mL.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

EXAMPLES

The exemplified compositions are shelf stable nutritional compositions prepared in accordance with the manufacturing methods described herein, such that each exemplified composition, unless otherwise specified, includes an aseptically processed embodiment and a retort packaged embodiment.

Examples 1-5

Prophetic examples 1-5 illustrate ready-to-feed nutritional emulsions, the ingredients of which are listed in the table below. All ingredient amounts listed are in kilograms, unless otherwise specified.

TABLE 7

Examples 1-5

| Ingredient | Ex. 1 | Ex. 2 | Ex. 3 | Ex. 4 | Ex. 5 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| lacto-N-neotetraose (LNnT) | 0.049 | 0.097 | 0.245 | 0.490 | 3.92 |
| Galactooligosaccharides (GOS) | 3.92 | 3.92 | 3.92 | 3.92 | 0 |
| Whey protein concentrate | 6.40 | 6.40 | 6.40 | 6.40 | 6.40 |

TABLE 7-continued

Examples 1-5

| Ingredient | Ex. 1 | Ex. 2 | Ex. 3 | Ex. 4 | Ex. 5 |
| --- | --- | --- | --- | --- | --- |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, D3, E, K1 premix | 47.4 g | 47.4 g | 47.4 g | 47.4 g | 47.4 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 6-10

Prophetic examples 6-10 illustrate ready-to-feed nutritional emulsions of the present disclosure, the ingredients of which are listed in the table below. All ingredient amounts listed are in kilograms, unless otherwise specified.

TABLE 8

Examples 6-10

| Ingredient | Ex. 6 | Ex. 7 | Ex. 8 | Ex. 9 | Ex. 10 |
| --- | --- | --- | --- | --- | --- |
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2'-fucosyllactos (2'FL) | 0.049 | 0.097 | 0.245 | 0.490 | 3.92 |
| Galactooligosaccharides (GOS) | 3.92 | 3.92 | 3.92 | 3.92 | 0 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |

TABLE 8-continued

Examples 6-10

| Ingredient | Ex. 6 | Ex. 7 | Ex. 8 | Ex. 9 | Ex. 10 |
|---|---|---|---|---|---|
| Choline chloride | 53.9 g | 53.9 g | 53.9 g | 53.9 g | 53.9 g |
| Vitamin A, D3, E, K1 premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 11-15

Prophetic examples 11-15 illustrate concentrated liquid emulsions, the ingredients of which are listed in the table below. All ingredient amounts listed are in kilograms, unless otherwise specified.

TABLE 9

Examples 11-15

| Ingredient | Ex. 11 | Ex. 12 | Ex. 13 | Ex. 14 | Ex. 15 |
|---|---|---|---|---|---|
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| lacto-N-neotetraose (LNnT) | 0.097 | 0.194 | 0.490 | 0.98 | 7.84 |
| Galactooligosaccharides (GOS) | 7.84 | 7.84 | 7.84 | 7.84 | 7.84 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, D3, E, K1 premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 16-20

Prophetic examples 16-20 illustrate ready-to-feed nutritional emulsions, the ingredients of which are listed in the table below. All ingredient amounts listed are in kilograms, unless otherwise specified.

TABLE 10

Examples 16-20

| Ingredient | Ex. 16 | Ex. 17 | Ex. 18 | Ex. 19 | Ex. 20 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 6' sialyllactose (6'SL) | 0.049 | 0.097 | 0.245 | 0.490 | 0.98 |
| 2'fucosyllactose (2'FL) | 0.049 | 0.097 | 0.245 | 0.490 | 0.98 |
| Lacto-N-neotetraose (LNnT) | 0.049 | 0.097 | 0.245 | 0.490 | 0.98 |
| Galactooligosaccharides (GOS) | 3.92 | 3.92 | 3.92 | 1.96 | 0.98 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |

TABLE 10-continued

Examples 16-20

| Ingredient | Ex. 16 | Ex. 17 | Ex. 18 | Ex. 19 | Ex. 20 |
|---|---|---|---|---|---|
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, D3, E, K1 premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 21-25

Prophetic examples 21-25 illustrate concentrated liquid emulsions, the ingredients of which are listed in the table below. All ingredient amounts listed are in kilograms, unless otherwise specified.

TABLE 11

Examples 21-25

| Ingredient | Ex. 21 | Ex. 22 | Ex. 23 | Ex. 24 | Ex. 25 |
|---|---|---|---|---|---|
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| 6' sialyllactose (6'SL) | 0.097 | 0.194 | 0.490 | 0.98 | 1.96 |
| 2'fucosyllactose (2'FL) | 0.097 | 0.194 | 0.490 | 0.98 | 1.96 |
| Lacto-N-neotetraose (LNnT) | 0.097 | 0.194 | 0.490 | 0.98 | 1.96 |
| Galactooligosaccharides (GOS) | 7.84 | 7.84 | 7.84 | 3.92 | 3.921 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |

TABLE 11-continued

Examples 21-25

| Ingredient | Ex. 21 | Ex. 22 | Ex. 23 | Ex. 24 | Ex. 25 |
|---|---|---|---|---|---|
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, D3, E, K1 premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 26-30

Prophetic examples 26-30 illustrate human milk fortifier liquids, the ingredients of which are listed in the table below. All ingredient amounts listed are in kilograms, unless otherwise specified.

TABLE 12

Examples 26-30

| Ingredient | Ex. 26 | Ex. 27 | Ex. 28 | Ex. 29 | Ex. 30 |
|---|---|---|---|---|---|
| Water | Q.S. | Q.S. | Q.S. | Q.S. | Q.S. |
| Non-fat milk | 353 | 353 | 353 | 353 | 353 |
| Corn Syrup Solids | 85.3 | 85.3 | 85.3 | 85.3 | 85.3 |
| Medium Chain Triglycerides | 53.2 | 53.2 | 53.2 | 53.2 | 53.2 |
| Whey Protein Concentrate | 47.2 | 47.2 | 47.2 | 47.2 | 47.2 |
| 6' sialyllactose (6'SL) | 0.049 | 0.097 | 0.245 | 0.490 | 1.96 |
| 2'fucosyllactose (2'FL) | 0.049 | 0.097 | 0.245 | 0.490 | 1.96 |
| Lacto-N-neotetraose (LNnT) | 0.049 | 0.097 | 0.245 | 0.490 | 1.96 |
| Calcium Phosphate | 25.5 | 25.5 | 25.5 | 25.5 | 25.5 |
| Ascorbic Acid | 5.6 | 5.6 | 5.6 | 5.6 | 5.6 |
| Potassium Citrate | 3.1 | 3.1 | 3.1 | 3.1 | 3.1 |
| Magnesium Chloride | 2.8 | 2.8 | 2.8 | 2.8 | 2.8 |
| Sodium Citrate | 1.4 | 1.4 | 1.4 | 1.4 | 1.4 |
| Sodium Chloride | 1.4 | 1.4 | 1.4 | 1.4 | 1.4 |
| Soy Lecithin | 609 g | 609 g | 609 g | 609 g | 609 g |
| M-Inositol | 500 g | 500 g | 500 g | 500 g | 500 g |
| Niacinamide | 400 g | 400 g | 400 g | 400 g | 400 g |
| ARA Oil | 313 g | 313 g | 313 g | 313 g | 313 g |
| Tocopherol Acetate | 310 g | 310 g | 310 g | 310 g | 310 g |
| Zinc Sulfate | 300 g | 300 g | 300 g | 300 g | 300 g |
| Calcium Pantothenate | 182 g | 182 g | 182 g | 182 g | 182 g |
| Ferrous Sulfate | 133 g | 133 g | 133 g | 133 g | 133 g |
| DHA Oil | 116 g | 116 g | 116 g | 116 g | 116 g |
| Vitamin A Palmitate | 100 g | 100 g | 100 g | 100 g | 100 g |
| Cupric Sulfate | 51.0 g | 51.0 g | 51.0 g | 51.0 g | 51.0 g |
| Thiamine Hydrochloride | 50.0 g | 50.0 g | 50.0 g | 50.0 g | 50.0 g |
| Riboflavin | 47.0 g | 47.0 g | 47.0 g | 47.0 g | 47.0 g |
| Pyridoxine Hydrochloride | 27.0 g | 27.0 g | 27.0 g | 27.0 g | 27.0 g |
| Vitamin D3 | 20.0 g | 20.0 g | 20.0 g | 20.0 g | 20.0 g |
| Folic Acid | 3.5 g | 3.5 g | 3.5 g | 3.5 g | 3.5 g |
| Biotin | 3.4 g | 3.4 g | 3.4 g | 3.4 g | 3.4 g |
| Manganous Sulfate | 1.5 g | 1.5 g | 1.5 g | 1.5 g | 1.5 g |
| Phylloquinone | 1.2 g | 1.2 g | 1.2 g | 1.2 g | 1.2 g |
| Cyanocobalamin | 100 mg | 100 mg | 100 mg | 100 mg | 100 mg |
| Sodium Selenate | 43.0 mg | 43.0 mg | 43.0 mg | 43.0 mg | 43.0 mg |

Examples 31-35

Prophetic examples 31-35 illustrate spray dried nutritional powders, the ingredients of which are listed in the table below. All ingredient amounts listed are in kilograms, unless otherwise specified.

TABLE 13

Examples 31-35

| Ingredient | Ex. 31 | Ex. 32 | Ex. 33 | Ex. 34 | Ex. 35 |
|---|---|---|---|---|---|
| Condensed Skim Milk | 698.5 | 698.5 | 698.5 | 698.5 | 698.5 |
| Lactose | 386.0 | 386.0 | 386.0 | 386.0 | 386.0 |
| High oleic safflower oil | 114.4 | 114.4 | 114.4 | 114.4 | 114.4 |
| Soybean oil | 85.51 | 85.51 | 85.51 | 85.51 | 85.51 |
| Coconut oil | 78.76 | 78.76 | 78.76 | 78.76 | 78.76 |
| Lacto-N-neotetraose (LNnT) | 0.385 | 0.770 | 1.925 | 3.85 | 30.8 |
| Galactooligosaccharides (GOS) | 30.8 | 30.8 | 30.8 | 30.8 | 0 |
| Whey protein concentrate | 51.08 | 51.08 | 51.08 | 51.08 | 51.08 |
| Potassium citrate | 9.168 | 9.168 | 9.168 | 9.168 | 9.168 |
| Calcium carbonate | 4.054 | 4.054 | 4.054 | 4.054 | 4.054 |
| Soy lecithin | 1.120 | 1.120 | 1.120 | 1.120 | 1.120 |
| ARA oil | 2.949 | 2.949 | 2.949 | 2.949 | 2.949 |
| Nucleotide/chloride premix | 2.347 | 2.347 | 2.347 | 2.347 | 2.347 |
| Potassium chloride | 1.295 | 1.295 | 1.295 | 1.295 | 1.295 |
| Ascorbic acid | 1.275 | 1.275 | 1.275 | 1.275 | 1.275 |
| Vitamin mineral premix | 1.116 | 1.116 | 1.116 | 1.116 | 1.116 |
| DHA oil | 1.113 | 1.113 | 1.113 | 1.113 | 1.113 |
| Magnesium chloride | 1.038 | 1.038 | 1.038 | 1.038 | 1.038 |
| Sodium chloride | 579.4 g | 579.4 g | 579.4 g | 579.4 g | 579.4 g |
| Ferrous sulfate | 453.6 g | 453.6 g | 453.6 g | 453.6 g | 453.6 g |
| Choline chloride | 432.1 g | 432.1 g | 432.1 g | 432.1 g | 432.1 g |
| Vitamin A, D3, E, K1 premix | 377.2 g | 377.2 g | 377.2 g | 377.2 g | 377.2 g |
| Ascorbyl Palmitate | 361.3 g | 361.3 g | 361.3 g | 361.3 g | 361.3 g |
| Mixed carotenoid premix | 350.1 g | 350.1 g | 350.1 g | 350.1 g | 350.1 g |
| Mixed Tocopherols | 159.2 g | 159.2 g | 159.2 g | 159.2 g | 159.2 g |
| L-carnitine | 26.30 g | 26.30 g | 26.30 g | 26.30 g | 26.30 g |
| Riboflavin | 3.181 g | 3.181 g | 3.181 g | 3.181 g | 3.181 g |
| Tricalcium phosphate | 0-5.23 | 0-5.23 | 0-5.23 | 0-5.23 | 0-5.23 |
| Potassium phosphate monobasic | 0-5.23 | 0-5.23 | 0-5.23 | 0-5.23 | 0-5.23 |
| Potassium hydroxide | AN | AN | AN | AN | AN |

AN = as needed

Examples 36-40

Prophetic examples 36-40 illustrate nutritional bars, the ingredients of which are listed in the table below. All ingredient amounts listed are in kilograms, unless otherwise specified.

TABLE 14

Examples 36-40

| Ingredient | Ex. 36 | Ex. 37 | Ex. 38 | Ex. 39 | Ex. 40 |
| --- | --- | --- | --- | --- | --- |
| Soy Crisps | 298.80 | 298.80 | 298.80 | 298.80 | 298.80 |
| Coating, Dark Chocolate | 196.90 | 196.90 | 196.90 | 196.90 | 196.90 |
| Corn Syrup | 177.90 | 177.90 | 177.90 | 177.90 | 177.90 |
| Milk Chocolate Drops | 54.80 | 54.80 | 54.80 | 54.80 | 54.80 |
| Marshmallow | 51.00 | 51.00 | 51.00 | 51.00 | 51.00 |
| Fructooligosaccharide Powder | 50.10 | 50.10 | 50.10 | 50.10 | 50.10 |
| Milk Protein Isolate Fonterra | 50.00 | 50.00 | 50.00 | 50.00 | 50.00 |
| High Oleic Sunflower Oil or High Oleic Safflower Oil | 32.40 | 32.40 | 32.40 | 32.40 | 32.40 |
| Glycerine | 23.20 | 23.20 | 23.20 | 23.20 | 23.20 |
| Corn Syrup | 18.00 | 18.00 | 18.00 | 18.00 | 18.00 |
| Crystalline Fructose | 14.70 | 14.70 | 14.70 | 14.70 | 14.70 |
| Vitamin/Mineral Premix | 13.20 | 13.20 | 13.20 | 13.20 | 13.20 |
| Flavor | 7.60 | 7.60 | 7.60 | 7.60 | 7.60 |
| Tricalcium Phosphate | 5.10 | 5.10 | 5.10 | 5.10 | 5.10 |
| Water | 3.50 | 3.50 | 3.50 | 3.50 | 3.50 |
| Flavor, Vanilla Natural | 1.00 | 1.00 | 1.00 | 1.00 | 1.00 |
| Xanthan Gum | 0.80 | 0.80 | 0.80 | 0.80 | 0.80 |
| MagNifique Glycerrhizinate | 0.70 | 0.70 | 0.70 | 0.70 | 0.70 |
| Soy Lecithin | 0.30 | 0.30 | 0.30 | 0.30 | 0.30 |
| lacto-N-neotetraose (LNnT) | 1.00 | 2.00 | 5.00 | 10.00 | 80.00 |

Examples 41-45

Prophetic examples 41-45 illustrate liquid formulations, the ingredients of which are listed in the table below. All ingredient amounts listed are in kilograms, unless otherwise specified.

TABLE 15

Examples 41-45

| Ingredient | Ex. 41 | Ex. 42 | Ex. 43 | Ex. 44 | Ex. 45 |
| --- | --- | --- | --- | --- | --- |
| Water | Q.S. | Q.S. | Q.S. | Q.S. | Q.S. |
| Fibersol 2 | 57.3 | 57.3 | 57.3 | 57.3 | 57.3 |
| Sucromalt | 29.1 | 29.1 | 29.1 | 29.1 | 29.1 |
| Acid Casein | 27.3 | 27.3 | 27.3 | 27.3 | 27.3 |
| Glycerine | 15.0 | 15.0 | 15.0 | 15.0 | 15.0 |
| Soy Protein Isolate | 14.1 | 14.1 | 14.1 | 14.1 | 14.1 |
| Fructose | 10.8 | 10.8 | 10.8 | 10.8 | 10.8 |
| High Oleic Safflower Oil | 10.8 | 10.8 | 10.8 | 10.8 | 10.8 |
| Canola Oil | 8.1 | 8.1 | 8.1 | 8.1 | 8.1 |
| Soy Oil | 6.8 | 6.8 | 6.8 | 6.8 | 6.8 |
| Calcium Caseinate | 4.4 | 4.4 | 4.4 | 4.4 | 4.4 |
| Maltrin M100 | 4.2 | 4.2 | 4.2 | 4.2 | 4.2 |
| 20% Potassium Citrate | 3.3 | 3.3 | 3.3 | 3.3 | 3.3 |
| Potassium Citrate | 661.6 g | 661.6 g | 661.6 g | 661.6 g | 661.6 g |
| Plant Sterol Esters | 3.2 | 3.2 | 3.2 | 3.2 | 3.2 |
| 20% Sodium Hydroxide | 2.9 | 2.9 | 2.9 | 2.9 | 2.9 |
| Calcium Phosphate | 2.8 | 2.8 | 2.8 | 2.8 | 2.8 |
| Magnesium Chloride | 2.4 | 2.4 | 2.4 | 2.4 | 2.4 |
| French Vanilla flavoring | 2.3 | 2.3 | 2.3 | 2.3 | 2.3 |
| Sodium Citrate | 1.5 | 1.5 | 1.5 | 1.5 | 1.5 |
| Soy Lecithin | 1.4 | 1.4 | 1.4 | 1.4 | 1.4 |
| Magnesium Phosphate | 1.0 | 1.0 | 1.0 | 1.0 | 1.0 |
| Artificial Vanilla | 1.0 | 1.0 | 1.0 | 1.0 | 1.0 |
| Potassium Chloride | 850.0 g | 850.0 g | 850.0 g | 850.0 g | 850.0 g |
| Potassium Phosphate | 800.0 g | 800.0 g | 800.0 g | 800.0 g | 800.0 g |
| Potassium Citrate | 688.4 g | 688.4 g | 688.4 g | 688.4 g | 688.4 g |
| Choline Chloride | 651.5 g | 651.5 g | 651.5 g | 651.5 g | 651.5 g |
| Ascorbic Acid | 584.1 g | 584.1 g | 584.1 g | 584.1 g | 584.1 g |
| Carrageenan | 500.0 g | 500.0 g | 500.0 g | 500.0 g | 500.0 g |
| 45% Potassium Hydroxide | 418.1 g | 418.1 g | 418.1 g | 418.1 g | 418.1 g |
| Ferrous Sulfate, Dried | 61.5 g | 61.5 g | 61.5 g | 61.5 g | 61.5 g |
| Zinc Sulfate, Monohydrate | 48.4 g | 48.4 g | 48.4 g | 48.4 g | 48.4 g |
| Niacinamide | 25.5 g | 25.5 g | 25.5 g | 25.5 g | 25.5 g |
| Calcium Pantothenate | 18.1 g | 18.1 g | 18.1 g | 18.1 g | 18.1 g |
| Chromium Picolinate, Anhydrous | 8.3 g | 8.3 g | 8.3 g | 8.3 g | 8.3 g |
| Manganese Sulfate, Monohydrate | 7.7 g | 7.7 g | 7.7 g | 7.7 g | 7.7 g |
| Cupric Sulfate, Anhydrous | 6.0 g | 6.0 g | 6.0 g | 6.0 g | 6.0 g |
| Pyridoxine Hydrochloride | 4.2 g | 4.2 g | 4.2 g | 4.2 g | 4.2 g |
| Thiamine Chloride Hydrochloride | 4.0 g | 4.0 g | 4.0 g | 4.0 g | 4.0 g |
| Riboflavin | 3.0 g | 3.0 g | 3.0 g | 3.0 g | 3.0 g |
| Folic Acid | 623.6 mg | 623.6 mg | 623.6 mg | 623.6 mg | 623.6 mg |
| Biotin | 476.5 mg | 476.5 mg | 476.5 mg | 476.5 mg | 476.5 mg |
| Sodium Molybdate, Dihydrate | 247.2 mg | 247.2 mg | 247.2 mg | 247.2 mg | 247.2 mg |
| Sodium Selenate, Anhydrous | 211.5 mg | 211.5 mg | 211.5 mg | 211.5 mg | 211.5 mg |
| Cyanocobalamin | 12.5 mg | 12.5 mg | 12.5 mg | 12.5 mg | 12.5 mg |
| Sucralose | 33.0 g | 33.0 g | 33.0 g | 33.0 g | 33.0 g |
| Acesulfame Potassium | 76.0 g | 76.0 g | 76.0 g | 76.0 g | 76.0 g |
| dl-Alpha-Tocopheryl Acetate | 54.5 g | 54.5 g | 54.5 g | 54.5 g | 54.5 g |
| Phylloquinone | 92.4 mg | 92.4 mg | 92.4 mg | 92.4 mg | 92.4 mg |

TABLE 15-continued

Examples 41-45

| Ingredient | Ex. 41 | Ex. 42 | Ex. 43 | Ex. 44 | Ex. 45 |
|---|---|---|---|---|---|
| Vitamin D3 | 13.2 mg | 13.2 mg | 13.2 mg | 13.2 mg | 13.2 mg |
| Vitamin A Palmitate | 4.5 g | 4.5 g | 4.5 g | 4.5 g | 4.5 g |
| Potassium Iodide | 220.5 mg | 220.5 mg | 220.5 mg | 220.5 mg | 220.5 mg |
| Vitamin B12 (86.4% Cyanocobalamin) | 31.7 mg | 31.7 mg | 31.7 mg | 31.7 mg | 31.7 mg |
| lacto-N-neotetraose (LNnT) | 0.392 | 1.96 | 3.92 | 7.84 | 15.68 |

Examples 46-50

Prophetic examples 46-50 illustrate liquid formulations, the ingredients of which are listed in the table below. All ingredient amounts listed are in kilograms, unless otherwise specified.

TABLE 16

Examples 46-50

| Ingredient | Ex. 46 | Ex. 47 | Ex. 48 | Ex. 49 | Ex. 50 |
|---|---|---|---|---|---|
| Water | Q.S. | Q.S. | Q.S. | Q.S. | Q.S. |
| Sugar | 87.7 | 87.7 | 87.7 | 87.7 | 87.7 |
| Corn maltodextrin | 70.7 | 70.7 | 70.7 | 70.7 | 70.7 |
| Milk protein concentrate | 26.2 | 26.2 | 26.2 | 26.2 | 26.2 |
| Soy oil | 13.4 | 13.4 | 13.4 | 13.4 | 13.4 |
| Soy protein isolate | 10.5 | 10.5 | 10.5 | 10.5 | 10.5 |
| Pea protein concentrate | 6.2 | 6.2 | 6.2 | 6.2 | 6.2 |
| Canola oil | 5.4 | 5.4 | 5.4 | 5.4 | 5.4 |
| Corn oil | 4.1 | 4.1 | 4.1 | 4.1 | 4.1 |
| Magnesium phosphate | 2.9 | 2.9 | 2.9 | 2.9 | 2.9 |
| Potassium citrate | 2.1 | 2.1 | 2.1 | 2.1 | 2.1 |
| Cellulose gel | 2.0 | 2.0 | 2.0 | 2.0 | 2.0 |
| Natural and artificial flavor | 2.0 | 2.0 | 2.0 | 2.0 | 2.0 |
| Calcium carbonate | 1.0 | 1.0 | 1.0 | 1.0 | 1.0 |
| Potassium chloride | 1.0 | 1.0 | 1.0 | 1.0 | 1.0 |
| Calcium phosphate | 960.0 g | 960.0 g | 960.0 g | 960.0 g | 960.0 g |
| Sodium citrate | 800.0 g | 800.0 g | 800.0 g | 800.0 g | 800.0 g |
| Salt | 710.0 g | 710.0 g | 710.0 g | 710.0 g | 710.0 g |
| Choline chloride | 480.0 g | 480.0 g | 480.0 g | 480.0 g | 480.0 g |
| Ascorbic acid | 468.7 g | 468.7 g | 468.7 g | 468.7 g | 468.7 g |
| Cellulose gum | 360.0 g | 360.0 g | 360.0 g | 360.0 g | 360.0 g |
| Monoglycerides | 286.6 g | 286.6 g | 286.6 g | 286.6 g | 286.6 g |
| Soy lecithin | 286.6 g | 286.6 g | 286.6 g | 286.6 g | 286.6 g |
| Carrageenan | 240.0 g | 240.0 g | 240.0 g | 240.0 g | 240.0 g |
| Potassium hydroxide | 145.4 g | 145.4 g | 145.4 g | 145.4 g | 145.4 g |
| Ferrous sulfate | 59.8 g | 59.8 g | 59.8 g | 59.8 g | 59.8 g |
| dl-alpha-tocopheryl acetate | 54.8 g | 54.8 g | 54.8 g | 54.8 g | 54.8 g |
| Zinc sulfate | 45.6 g | 45.6 g | 45.6 g | 45.6 g | 45.6 g |
| Niacinamide | 25.9 g | 25.9 g | 25.9 g | 25.9 g | 25.9 g |
| Manganese sulfate | 17.6 g | 17.6 g | 17.6 g | 17.6 g | 17.6 g |
| Calcium pantothenate | 16.7 g | 16.7 g | 16.7 g | 16.7 g | 16.7 g |
| Cupric sulfate | 9.2 g | 9.2 g | 9.2 g | 9.2 g | 9.2 g |
| Vitamin A palmitate | 4.3 g | 4.3 g | 4.3 g | 4.3 g | 4.3 g |
| Thiamine chloride hydrochloride | 4.3 g | 4.3 g | 4.3 g | 4.3 g | 4.3 g |
| Pyridoxine hydrochloride | 4.1 g | 4.1 g | 4.1 g | 4.1 g | 4.1 g |
| Riboflavin | 3.3 g | 3.3 g | 3.3 g | 3.3 g | 3.3 g |
| Folic acid | 580.0 mg | 580.0 mg | 580.0 mg | 580.0 mg | 580.0 mg |
| Chromium chloride | 561.0 mg | 561.0 mg | 561.0 mg | 561.0 mg | 561.0 mg |
| Biotin | 504.0 mg | 504.0 mg | 504.0 mg | 504.0 mg | 504.0 mg |
| Sodium molybdate | 441.0 mg | 441.0 mg | 441.0 mg | 441.0 mg | 441.0 mg |
| Potassium iodide | 207.0 mg | 207.0 mg | 207.0 mg | 207.0 mg | 207.0 mg |
| Sodium selenate | 195.0 mg | 195.0 mg | 195.0 mg | 195.0 mg | 195.0 mg |
| Phylloquinone | 81.3 mg | 81.3 mg | 81.3 mg | 81.3 mg | 81.3 mg |
| Vitamin D3 | 13.3 mg | 13.3 mg | 13.3 mg | 13.3 mg | 13.3 mg |
| Cyanocobalamin | 11.4 mg | 11.4 mg | 11.4 mg | 11.4 mg | 11.4 mg |
| 2'fucosyllactose (2'FL) | 0.392 | 1.96 | 3.92 | 7.84 | 15.68 |

Example 51

Fecal samples from eight human babies, one group of four breast-fed and the other group of four formula-fed, were used as inocula for anaerobic fermentation (37° C.) of lacto-N-neotetraose (LNnT) and 2'-fucosyllactose. Supernatants from the fermentation cultures were sampled at 0 hr, 3 hr, and 6 hr. A culture without addition of HMOs served as a control. A sample of the fermentation medium (blank), which constituted approximately 90% of the starting culture volume, was also analyzed.

Samples were extracted and split into equal parts for analysis on GC/MS and LC/MS/MS platforms. Agmatine ions were identified in chromatograms, and peak area was integrated for quantitative analysis. The resulting data in tables 1 and 2 shows the relative ratios of agmatine compared to the blank for both breast fed and formula fed infants.

While the present disclosure has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A method of providing a neuroprotective effect to an individual in need thereof, the method comprising administration of a synthetic composition comprising at least one human milk oligosaccharide as an active ingredient, wherein the human milk oligosaccharide is selected from lacto-N-neotetraose and 2'-fucosyllactose;
    wherein a level of agmatine in the individual is increased by administration of the synthetic composition;
    wherein the synthetic composition does not comprise lacto-N-neohexaose;
    wherein the synthetic composition comprises protein in an amount of 7% to 40% of the total calories in the synthetic composition, fat, and carbohydrate in addition to the at least one human milk oligosaccharide;
    wherein the individual in need thereof is selected from the group consisting of: an infant born severely prematurely; an infant suffering from severe lung disease, heart disease, a serious infection, trauma to the brain, trauma to the skull, a congenital malformation of the brain, or hypotension; an adult who has undergone cardiac arrest, respiratory arrest, near-drowning, or near-hanging; an adult who has suffered a form of incomplete suffocation; and an adult who has suffered a non-hemorrhagic stroke.

2. The method of claim 1, wherein the composition further comprises a dietary oligosaccharide selected from galactooligosaccharides, inulin, 6'-sialyllactose, lacto-N-tetraose, disialylated lacto-N-tetraose, 3'-fucosyllactose, or 3'-sialyllactose.

3. The method of claim 1, wherein the at least one human milk oligosaccharide is lacto-N-neotetraose.

4. The method of claim 1, wherein the at least one human milk oligosaccharide is 2'-fucosyllactose.

5. The method of claim 1, wherein the composition is a liquid and comprises from about 0.001 mg/mL to about 10 mg/mL of the human milk oligosaccharide.

6. The method of claim 1, wherein the composition is a liquid and comprises from about 0.001 mg/mL to about 5 mg/mL of the human milk oligosaccharide.

7. The method of claim 1, wherein the composition is a powder and comprises from about 0.0005% to about 5% of the human milk oligosaccharide by weight of the powder.

8. The method of claim 1, wherein the composition is a powder and comprises from about 0.01% to about 1% of the human milk oligosaccharide by weight of the powder.

9. The method of claim 1, wherein the composition is an infant formula.

10. The method of claim 1, wherein the composition is an adult nutritional formula.

11. The method of claim 1, wherein the composition is a nutritional bar, nutritional liquid, or nutritional powder.

12. A method of treating hypoxic-ischemic brain injury in an individual, the method comprising administration of a synthetic composition comprising at least one human milk oligosaccharide selected from lacto-N-neotetraose and 2'-fucosyllactose;
    wherein the synthetic composition comprises protein in an amount of 7% to 40% of the total calories in the synthetic composition, fat, and carbohydrate in addition to the at least one human milk oligosaccharide;
    wherein the synthetic composition does not comprise lacto-N-neohexaose;
    wherein the individual is selected from the group consisting of: an infant born severely prematurely; an infant suffering from severe lung disease, heart disease, a serious infection, trauma to the brain, trauma to the skull, a congenital malformation of the brain, or hypotension; an adult who has undergone cardiac arrest, respiratory arrest, near-drowning, or near-hanging; an adult who has suffered a form of incomplete suffocation; and an adult who has suffered a non-hemorrhagic stroke.

13. The method of claim 12, wherein the at least one human milk oligosaccharide is lacto-N-neotetraose.

14. The method of claim 12, wherein the at least one human milk oligosaccharide is 2'-fucosyllactose.

15. The method of claim 12, wherein the composition is a liquid and comprises from about 0.001 mg/mL to about 10 mg/mL of the human milk oligosaccharide.

16. The method of claim 12, wherein the composition is a liquid and comprises from about 0.001 mg/mL to about 5 mg/mL of the human milk oligosaccharide.

17. The method of claim 12, wherein the composition is a powder and comprises from about 0.0005% to about 5% of the human milk oligosaccharide by weight of the powder.

18. The method of claim 12, wherein the composition is a powder and comprises from about 0.01% to about 1% of the human milk oligosaccharide by weight of the powder.

19. A method of reducing at least one of nitric oxide synthase associated hypoxic-ischemic brain injury and N-methyl-D-aspartate associated hypoxic-ischemic brain injury in an individual in need thereof, the method comprising administration of a nutritional composition comprising at least one human milk oligosaccharide in an amount of 0.001 mg/mL to about 5 mg/mL and selected from lacto-N-neotetraose and 2'-fucosyllactose;
    wherein the synthetic composition does not comprise lacto-N-neohexaose;
    wherein the synthetic composition comprises protein in an amount of 7% to 40% of the total calories in the synthetic composition, fat, and carbohydrate in addition to the at least one human milk oligosaccharide.

* * * * *